US012629416B2

(12) United States Patent (10) Patent No.: US 12,629,416 B2
Swoboda (45) Date of Patent: May 19, 2026

(54) ADJUVANT COMPOSITION FOR A VACCINE

(71) Applicant: TOTALENERGIES ONETECH, Courbevoie (FR)

(72) Inventor: Benjamin Swoboda, Orgeval (FR)

(73) Assignee: TOTALENERGIES ONETECH, Courbevoie (FR)

( * ) Notice: Subject to any disclaimer, the term of this patent is extended or adjusted under 35 U.S.C. 154(b) by 1252 days.

(21) Appl. No.: 17/430,554

(22) PCT Filed: Feb. 13, 2020

(86) PCT No.: PCT/FR2020/050267
§ 371 (c)(1),
(2) Date: Aug. 12, 2021

(87) PCT Pub. No.: WO2020/169903
PCT Pub. Date: Aug. 27, 2020

(65) Prior Publication Data
US 2022/0125918 A1 Apr. 28, 2022

(30) Foreign Application Priority Data
Feb. 18, 2019 (FR) ...................................... 1901614

(51) Int. Cl.
*A61K 39/39* (2006.01)
*A61K 39/00* (2006.01)

(52) U.S. Cl.
CPC .... *A61K 39/39* (2013.01); *A61K 2039/55566* (2013.01)

(58) Field of Classification Search
None
See application file for complete search history.

(56) References Cited

U.S. PATENT DOCUMENTS

| 2006/0233831 A1 | 10/2006 | Parisot et al. |
| 2010/0233196 A1 | 9/2010 | Dupuis et al. |
| 2019/0060192 A1 | 2/2019 | Swoboda |

FOREIGN PATENT DOCUMENTS

| EP | 0 343 548 A2 | 11/1989 | |
| EP | 3 095 839 A1 | 11/2016 | |
| EP | 3 143 981 A1 | 3/2017 | |
| FR | 2 922 767 A1 | 5/2009 | |
| RU | 2 072 868 C1 | 2/1997 | |
| WO | WO2005-009462 A2 | 2/2005 | |
| WO | WO-2016185046 A1 * | 11/2016 | ............. C10G 65/02 |

OTHER PUBLICATIONS

Stone, H.D., et al. "Preparation of inactivated oil-emulsion vaccines with avian viral or mycoplasma antigens." Avian diseases (1978): 666-674. (Year: 1978).*
Sheng, J.J. "Mineral Oil." in Handbook of Pharmaceutical Excipients (6th Edition) 2009: 445-447. (Year: 2009).*
Rimaniol et al., "In vitro interactions between macrophages and aluminum-containing adjuvants", Vaccine, Sep. 17, 2007, vol. 25, No. 37-38, pp. 6784-6792, XP022227074, abstract only.
English translation of the Chinese Office Action for Chinese Application No. 202080013930.4, dated Feb. 24, 2024.
International Search Report, issued in PCT/FR2020/050267, dated May 13, 2020.
Rimaniol, "In vitro interactions between macrophages and aluminum-containing adjuvants", Vaccine, 2007, vol. 25, pp. 6784-6792, XP022227074.
Written Opinion of the International Searching Authority for International Application No. PCT/FR2020/050267, dated May 13, 2020.

* cited by examiner

*Primary Examiner* — Bethany P Barham
*Assistant Examiner* — Peter Anthopolos
(74) *Attorney, Agent, or Firm* — DUANE MORRIS LLP; Gregory M. Lefkowitz

(57) ABSTRACT
An adjuvant composition for a vaccine includes one or more substantially isoparaffinic hydrocarbon oils having C17 and/or C18 isoparaffins, and one or more surfactants. A vaccine includes the adjuvant composition.

15 Claims, 2 Drawing Sheets

[Fig. 1]
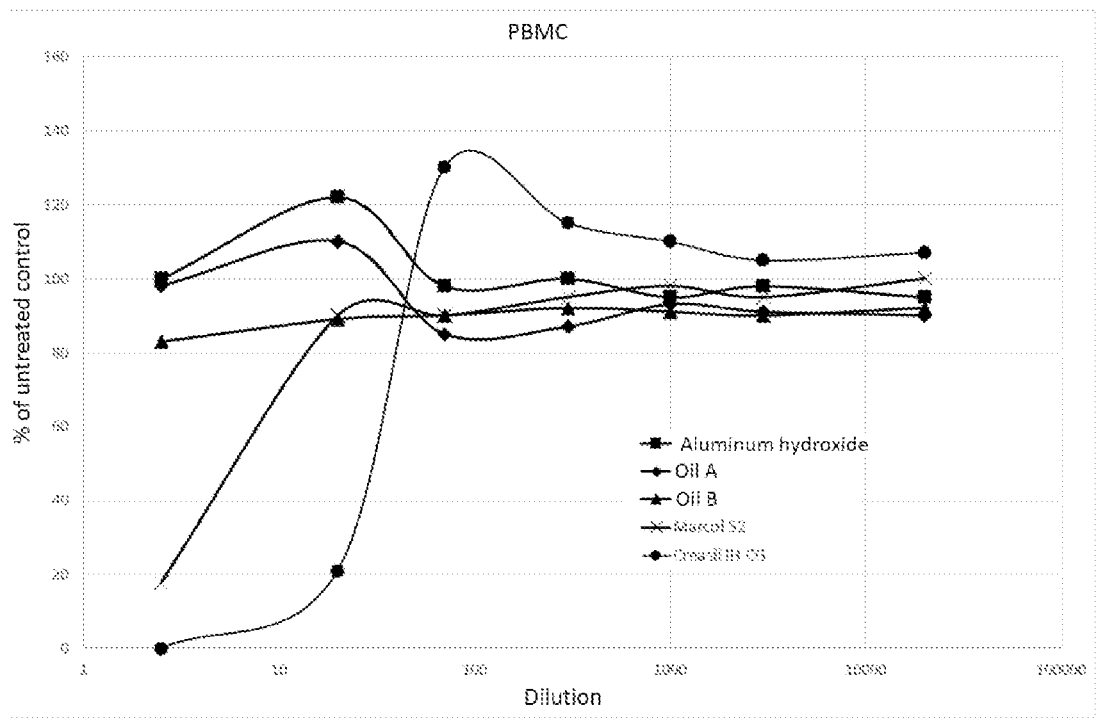
[Fig. 2]
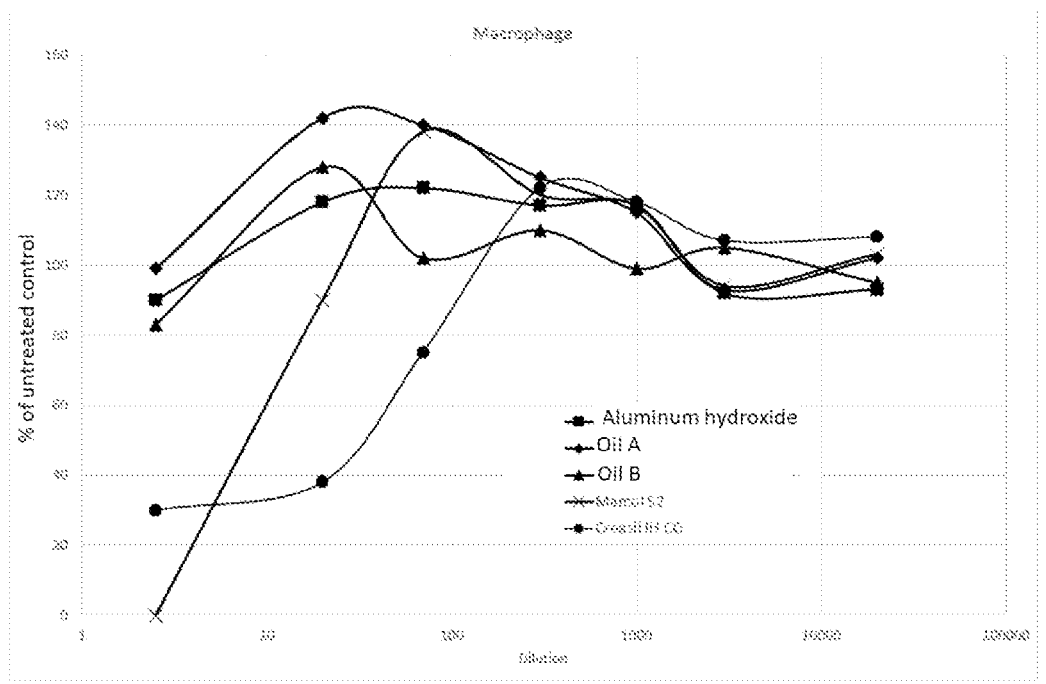

[Fig. 3]
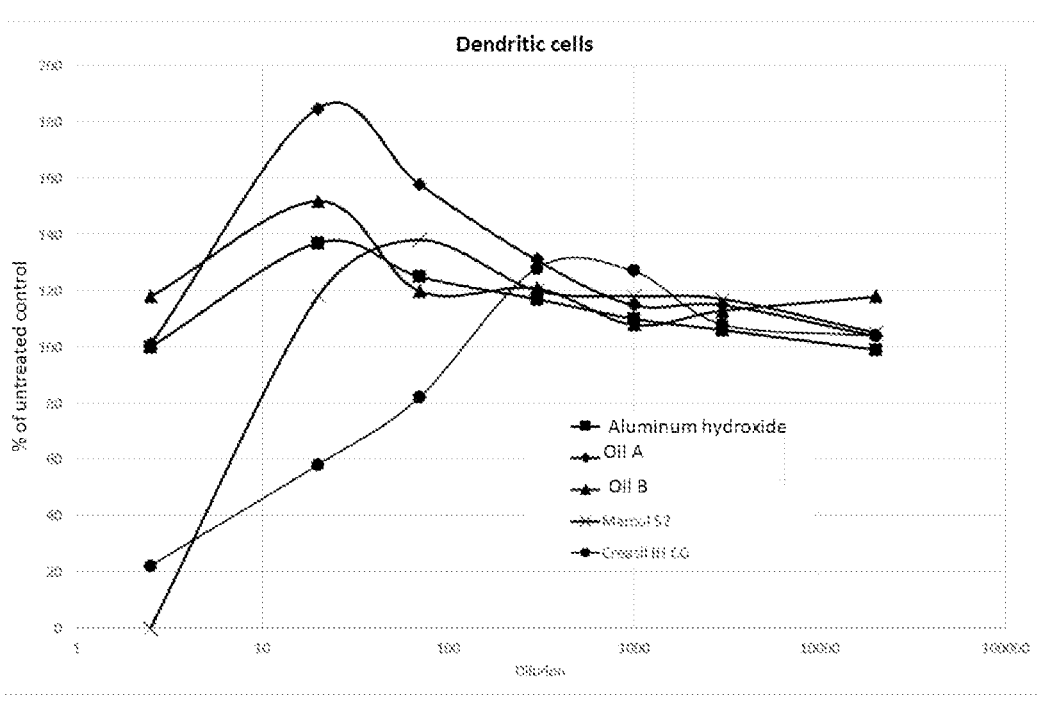

ADJUVANT COMPOSITION FOR A VACCINE

FIELD OF THE INVENTION

The present invention relates to a novel adjuvant composition for a vaccine comprising a predominantly isoparaffinic hydrocarbon oil and a surfactant.

TECHNICAL BACKGROUND OF THE INVENTION

Various different vaccine technologies currently exist, including so-called "live virus" vaccines (live antigens), so-called "attenuated virus" vaccines or so-called "inactivated virus" (inactivated antigen) vaccines.

In live virus vaccines, it is not necessary to add an adjuvant because they already have a sufficient level of efficacy. However, the risk of adverse effects associated with this type of vaccine is significant.

Conversely, since attenuated or inactivated virus vaccines have limited efficacy the use of an adjuvant is required. When the attenuated or inactivated virus, dissolved in water, is dispersed in an oil, the efficacy thereof is greatly increased. This dispersion, referred to as an emulsion, must be stable and as fluid as possible: stable in order to ensure proper preservation of the vaccine, and fluid so as to be able to be injected rapidly and painlessly. The oil thus acts as an adjuvant.

The reference oil used as a vaccine adjuvant is a white oil marketed under the brand name Marcol™ 52, constituted of paraffins and naphthenic compounds.

The document FR 2 922 767 discloses the use, in an adjuvant composition for a vaccine, of various oils derived from mineral, plant or animal origin as well as synthetic oils. This document discloses, among other relevant items, the Marcol™ 52 white oil and an isohexadecane corresponding to the commercial product Creasil® IH CG. These oils are formulated with surfactants in the vaccine adjuvants.

These oils present the drawback of having a certain cytotoxicity with respect to immune cells such as mononuclear cells isolated from peripheral blood (peripheral blood mononuclear cells or PBMC), macrophages and dendritic cells.

The document RU2072868 proposes an oil as adjuvant for a vaccine comprising a mixture of naphthenes, aromatic compounds and isoparaffins. This document teaches a maximum amount of 20% by weight of isoparaffins in order to lower reactogenicity.

The nature of the adjuvant oil may also have an effect on the immune response of the subject being treated. The present invention thus aims to provide a vaccine adjuvant that induces a strong immune response as well as the lowest possible cytotoxicity.

SUMMARY OF THE INVENTION

These objectives are achieved by virtue of a novel adjuvant composition.

The invention relates to an adjuvant composition for a vaccine comprising, relative to the total weight of the adjuvant composition:

at least 40% by weight of hydrocarbon oil comprising a content by weight of isoparaffins ranging from 90 to 100% relative to the total weight of the hydrocarbon oil, said isoparaffins including isoparaffins having 17 carbon atoms or 18 carbon atoms; and from 1 to 15% by weight of one or more surfactant(s).

According to one embodiment, said isoparaffins comprise, relative to the total weight of isoparaffins, at least 2% by weight of isoparaffins having 17 carbon atoms and/or isoparaffins having 18 carbon atoms.

According to one embodiment, the hydrocarbon oil comprises:

isoparaffins having 15 carbon atoms and isoparaffins having 16 carbon atoms, in a combined amount ranging from 80 to 95% by weight, relative to the total weight of the hydrocarbon oil; or isoparaffins having 15 carbon atoms and isoparaffins having 16 carbon atoms, in a combined amount ranging from 40 to 80% by weight, relative to the total weight of the hydrocarbon oil; or isoparaffins having 16 carbon atoms, isoparaffins having 17 carbon atoms, and isoparaffins having 18 carbon atoms, in a combined amount ranging from 80 to 98% by weight, relative to the total weight of the hydrocarbon oil; or isoparaffins having 17 carbon atoms and isoparaffins having 18 carbon atoms, in a combined amount ranging from 80 to 98% by weight, relative to the total weight of the hydrocarbon oil.

According to one embodiment, the surfactant is selected from among non-ionic surfactants, preferably sorbitan esters, preferably sorbitan fatty acid esters, preferably the surfactant is a sorbitan monooleate.

According to one embodiment, the composition of the invention comprises, relative to the total weight of the composition:

from 60 to 98% by weight of hydrocarbon oil comprising a content by weight of isoparaffins ranging from 95 to 100% relative to the total weight of the hydrocarbon oil, said isoparaffins including isoparaffins having 17 carbon atoms and/or 18 carbon atoms; and from 2 to 10% by weight of one or more surfactant(s).

The present invention also relates to a vaccine comprising the adjuvant composition according to the invention and at least one antigen.

According to one embodiment, the vaccine is in the form of a water-in-oil emulsion.

According to one embodiment, the mass ratio between the aqueous phase and the fatty phase of the water-in-oil emulsion ranges from 50/50 to 10/90, preferably from 40/60 to 20/80, and more preferentially is 30/70.

The present invention also relates to the use of an adjuvant composition according to the invention for reducing the cytotoxicity of a vaccine comprising said adjuvant composition.

The present invention also relates to the use of the hydrocarbon oil defined according to the invention, in an adjuvant composition for a vaccine, for reducing the cytotoxicity of the vaccine comprising said adjuvant composition.

The present invention also relates to the use of the hydrocarbon oil defined according to the invention, in an adjuvant composition for a vaccine, for enhancing the stability of the vaccine, in particular for a vaccine in the form of an emulsion.

The adjuvant composition according to the invention makes it possible to obtain a composition for a vaccine that exhibits very low cytotoxicity while also inducing the immune cells to produce a strong anti-infectious response.

The adjuvant composition according to the invention makes it possible to prepare vaccines that are indeed both stable and fluid.

FIGURES

FIG. 1 Effects of oils on the viability and activation of PBMCs, in the absence of parallel antigenic stimulation.

FIG. 2 Effects of oils on the viability and activation of macrophages, in the absence of parallel antigenic stimulation.

FIG. 3 Effects of oils on the viability and activation of dendritic cells, in the absence of parallel antigenic stimulation.

DETAILED DESCRIPTION OF THE INVENTION

The invention relates to an adjuvant composition for a vaccine comprising, relative to the total weight of the adjuvant composition:

at least 40% by weight of hydrocarbon oil comprising a content by weight of isoparaffins ranging from 90 to 100% relative to the total weight of the hydrocarbon oil, said isoparaffins including isoparaffins having 17 carbon atoms and/or 18 carbon atoms; and from 1 to 15% by weight of one or more surfactant(s).

As a preliminary matter, it should be noted that, in the description and the claims that follow, the term "comprised between" should be understood as including the limits mentioned.

Hydrocarbon Oil

Within the context and scope of the present invention, the hydrocarbon oil comprises a content by weight of isoparaffins ranging from 90 to 100% relative to the total weight of the hydrocarbon oil. Still within the context and scope of the present invention, the isoparaffins of the hydrocarbon oil include isoparaffins having 17 carbon atoms and/or isoparaffins having 18 carbon atoms.

According to one embodiment of the invention, the hydrocarbon oil used in the adjuvant composition comprises between 90 and 100% by weight of isoparaffins relative to the total weight of the hydrocarbon oil, said isoparaffins including, relative to the total weight of the isoparaffins, at least 2% by weight of isoparaffins having 17 carbon atoms and/or isoparaffins having 18 carbon atoms.

According to one embodiment of the invention, the hydrocarbon oil of the adjuvant composition comprises a content by weight of isoparaffins that is greater than or equal to 95%, and advantageously greater than or equal to 98% relative to the total weight of the hydrocarbon oil, said isoparaffins including, relative to the total weight of the isoparaffins, at least 2% by weight of isoparaffins having 17 carbon atoms and/or isoparaffins having 18 carbon atoms.

According to one embodiment of the invention, the hydrocarbon oil of the adjuvant composition comprises a content by weight of isoparaffins that is greater than or equal to 95%, and advantageously greater than or equal to 98% relative to the total weight of the hydrocarbon oil, said isoparaffins including, relative to the total weight of the isoparaffins, at least 20% by weight of isoparaffins having 17 carbon atoms and/or isoparaffins having 18 carbon atoms.

According to one embodiment of the invention, the isoparaffins contained in the hydrocarbon oil include, relative to the total weight of the isoparaffins, at least 20% by weight, preferably at least 30% by weight, preferably at least 35% by weight, preferably at least 40% by weight, preferably at least 60% by weight, preferably at least 80% by weight of isoparaffins having 17 carbon atoms and/or isoparaffins having 18 carbon atoms.

According to one embodiment of the invention, the hydrocarbon oil of the adjuvant composition comprises a content by weight of isoparaffins that is greater than or equal to 95%, and advantageously greater than or equal to 98% relative to the total weight of the hydrocarbon oil; and at least 90%, preferably at least 95%, by weight of said isoparaffins, relative to the total weight of the isoparaffins present in the hydrocarbon oil, contain from 12 to 30 carbon atoms, preferably from 13 to 19 carbon atoms, even more preferably from 14 to 18 carbon atoms.

According to one embodiment of the invention, the hydrocarbon oil comprises:

isoparaffins having 15 carbon atoms and isoparaffins having 16 carbon atoms, in a combined amount ranging from 40 to 80% by weight, preferably from 50 to 70% by weight, relative to the total weight of the hydrocarbon oil; or isoparaffins having 15 carbon atoms and isoparaffins having 16 carbon atoms, in a combined amount ranging from 80 to 95% by weight, relative to the total weight of the hydrocarbon oil; or isoparaffins having 16 carbon atoms, isoparaffins having 17 carbon atoms and isoparaffins having 18 carbon atoms, in a combined amount ranging from 80 to 98% by weight, relative to the total weight of the hydrocarbon oil; or isoparaffins having 17 carbon atoms and isoparaffins having 18 carbon atoms, in a combined amount ranging from 80 to 98% by weight, relative to the total weight of the hydrocarbon oil.

According to one embodiment of the invention, the isoparaffins are non-cyclic isoparaffins.

The hydrocarbon oil used in the adjuvant composition according to the invention preferably comprises a normal paraffin content of less than or equal to 10% by weight, preferably less than or equal to 5% by weight, and advantageously less than or equal to 2% by weight, relative to the total weight of the hydrocarbon oil.

According to one embodiment, the hydrocarbon oil according to the invention preferably comprises, relative to the total weight of the hydrocarbon oil, an isoparaffin content ranging from 90 to 100% by weight and a normal paraffin content ranging from 0 to 10% by weight, preferentially from 95 to 100% by weight of isoparaffins and from 0 to 5% by weight of normal paraffins and more preferentially from 98% to 100% by weight of isoparaffins and from 0 to 2% by weight normal paraffins. In an even more advantageous manner, the hydrocarbon oil of the adjuvant composition according to the invention does not contain normal paraffins.

The hydrocarbon oil of the adjuvant composition according to the invention preferably comprises a content of naphthenic compounds less than or equal to 1% by weight, preferentially less than or equal to 0.5% by weight, and more preferentially less than or equal to 100 ppm in weight, relative to the total weight of the hydrocarbon oil.

The hydrocarbon oil used in the adjuvant composition according to the invention is advantageously free of aromatic compounds. For example, this is understood to indicate a content by weight of aromatic compounds less than or equal to 500 ppm, preferably less than or equal to 300 ppm, preferentially less than or equal to 100 ppm, more preferentially less than or equal to 50 ppm, and advantageously less than or equal to 20 ppm measured for example by UV spectrometry.

According to one embodiment of the invention, the hydrocarbon oil comprises:

a content of isoparaffins ranging from 90 to 100% by weight, preferably from 95 to 100% by weight, and preferentially from 98% to 100% by weight, relative to the total weight of the hydrocarbon oil, said isoparaffins including, relative to the total weight of the isoparaffins, at least 2% by weight and preferentially at least 20% by weight, of isoparaffins having 17 carbon atoms and/or of isoparaffins having 18 carbon atoms, a content of normal paraffins less than or equal to 10% by weight, preferably less than or equal to 5% by weight, and preferentially less than or equal to 2% by weight, relative to the total weight of the hydrocarbon oil; and/or a content of naphthenic compounds less than or equal to 1% by weight, preferably less than or equal to 0.5% by weight, and preferentially less than or equal to 100 ppm, relative to the total weight of the hydrocarbon oil; and/or a content by weight of aromatic compounds less than or equal to 500 ppm, preferably less than or equal to 300 ppm, preferentially less than or equal to 100 ppm, more preferentially less than or equal to 50 ppm, and advantageously less than or equal to 20 ppm, relative to the total weight of the hydrocarbon oil.

The content by weight levels of isoparaffins, normal paraffins, naphthenes and aromatics in the hydrocarbon oil may be determined according to methods well known to the person skilled in the art. Mention may be made, by way of non-limiting example, of a gas chromatography method.

The hydrocarbon oil used in the adjuvant composition according to the invention also preferably has an extremely low content by weight of sulfur compounds, typically less than or equal to 5 ppm, preferentially less than or equal to 3 ppm, and more preferably less than or equal to at 0.5 ppm, that is to say at a level too low to be detected by means of conventional low-sulfur analysers.

According to one embodiment of the invention, the hydrocarbon oil has a boiling point ranging from 230 to 340° C., preferably from 235 to 330° C. and more preferentially from 240 to 325° C. according to the standard ASTM D86.

According to one embodiment of the invention, the difference between the final boiling point and the initial boiling point according to the standard ASTM D86 for hydrocarbon oil is less than 80° C., preferably less than 60° C., and more preferentially less than 40° C.

The hydrocarbon oil used in the adjuvant composition according to the invention also preferably has a flash point greater than or equal to 110° C., preferentially greater than or equal to 120° C., and more preferentially greater than or equal to 140° C. according to the standard EN ISO 2719. A high flash point, typically greater than 110° C., that makes it possible among other things to overcome safety problems during storage and transport by avoiding excessive flammability of the hydrocarbon oil.

The hydrocarbon oil also preferably has a vapour pressure at 20° C. less than or equal to 0.01 kPa.

According to one embodiment, the hydrocarbon oil used in the adjuvant composition according to the invention has a flash point greater than or equal to 110° C. according to the standard EN ISO 2719 and a vapour pressure at 20° C. less than or equal at 0.01 kPa. Preferentially the hydrocarbon oil has a flash point greater than or equal to 120° C. and a vapour pressure at 20° C. less than or equal to 0.01 kPa. And more preferentially, it has a flash point greater than or equal to 140° C. and a vapour pressure at 20° C. less than or equal to 0.01 kPa.

According to one embodiment of the invention, the hydrocarbon oil is of biological origin and typically has a biomaterial content of at least 90% by weight relative to the total weight of the hydrocarbon oil. This content level is advantageously higher, in particular greater than or equal to 95% by weight, preferably greater than or equal to 98% by weight, and advantageously equal to 100%. The determination of the biomaterial or bio-carbon content level is given in accordance with the standards ASTM D 6866-12, method B (ASTM D 6866-06) and ASTM D 7026 (ASTM D 7026-04).

The hydrocarbon oil of the adjuvant composition according to the invention also preferably has a kinematic viscosity at 40° C. less than or equal to 5 cSt, preferentially less than or equal to 4 cSt, and more preferentially less than or equal to 3 cSt according to the standard. EN ISO 3104.

The term "bio-carbon" indicates that the carbon is derived from a natural source and comes from a biomaterial, as indicated here below. The bio-carbon content and biomaterial content are terms that indicate the same value. A material derived from a renewable source or biomaterial is an organic material in which the carbon is derived from $CO_2$ recently fixed (on a human scale) by photosynthesis from the atmosphere. A biomaterial (100% carbon of natural origin) has a $^{14}C/^{12}C$ isotopic ratio greater than $10^{-12}$, typically around $1.2 \times 10^{-12}$, while a fossil material has a zero ratio. In fact, the isotope $^{14}C$ is formed in the atmosphere and is then integrated by photosynthesis, according to a time scale of a few decades at most. The half-life of $^{14}C$ is 5730 years. Thus, the materials resulting from photosynthesis, that is to say plants in general terms, necessarily have a maximum isotope $^{14}C$ content.

According to one embodiment of the invention, the hydrocarbon oil has a biodegradability at 28 days of at least 60%, preferably at least 70%, preferentially at least 75%, and even more preferentially at least 80%, as measured according to the Organisation for Economic Cooperation and Development's standard OECD 306.

According to one particular embodiment, the hydrocarbon oil has:

a boiling temperature ranging from 230 to 340° C., preferably from 235 to 330° C. and more preferentially from 240 to 325° C. in accordance with the standard ASTM D86; and/or a difference between the final boiling point and the initial boiling point in accordance with the standard ASTM D86 for hydrocarbon oil of less than 80° C., preferably less than 60° C., and more preferentially less than 40° C., and/or a biodegradability at 28 days of at least 60%, preferably at least 70%, preferentially at least 75%, and even more preferentially at least 80%, as measured according to the OECD standard 306; and/or a flash point greater than or equal to 110° C. according to the standard EN ISO 2719.

According to one particular embodiment of the invention, the hydrocarbon oil_of the adjuvant composition has a boiling range (measured in accordance with the standard ASTM D86) in the range from 235 to 330° C., and more preferentially from 240 to 325° C., and comprises a content by weight of isoparaffins that is greater than or equal at 95%, and advantageously greater than or equal to 98%, relative to the total weight of the hydrocarbon oil, said isoparaffins including, relative to the total weight of the isoparaffins, at least 2% by weight, preferably at least 20% by weight, of isoparaffins having 17 carbon atoms and/or isoparaffins having 18 carbon atoms.

Method for Obtaining the Hydrocarbon Oil

The hydrocarbon oil according to the invention may be a hydrocarbon fraction derived, for example, from the conversion of biomass. The term "derived from the conversion of biomass" is understood to refer to a hydrocarbon fraction produced from raw materials originating from biological sources.

Preferably, the hydrocarbon fraction derived from a biological source is obtained by means of a method comprising the steps of hydrodeoxygenation (HDO) and isomerisation (ISO). The hydrodeoxygenation (HDO) step leads: to the decomposition of the structures of biological esters or triglyceride constituents; to the elimination of oxygenated, phosphorous and sulfur compounds; and to the hydrogenation of olefinic bonds. The product resulting from the hydrodeoxygenation reaction is subsequently isomerised. A fractionation step may preferably follow the hydrodeoxygenation and isomerisation steps. In an advantageous manner, the fractions of interest are thereafter subjected to the steps of hydrotreatment and then distillation in order to obtain the specifications of the desired hydrocarbon oil according to the invention.

This HDO/ISO method is implemented on a crude bio-based feedstock, also referred to as biomass or raw material of biological origin, selected from the group consisting of plant oils, animal fats, fish oils and the mixtures thereof. Suitable raw materials of biological origin are for example rapeseed oil, canola oil, tall oil, sunflower oil, soybean oil, hemp oil, olive oil, linseed oil, mustard oil, palm oil, peanut oil, castor oil, coconut oil; animal fats such as tallow; recycled dietary fats; raw materials derived from genetic engineering; and biological feedstocks or raw materials produced from microorganisms such as algae and bacteria. Condensation products, esters or other derivatives obtained from crude biological materials may also serve as raw materials.

Preferably, the raw material of biological origin is an ester or a triglyceride derivative. This material is first of all subjected to a hydrodeoxygenation (HDO) step in order to decompose the structure of the constituent triglycerides or esters and to eliminate the oxygenated, phosphorous and sulfur compounds in a concomitant manner with the hydrogenation of the olefinic bonds. This hydrodeoxygenation (HDO) step of hydrodeoxygenating the raw material of biological origin is followed by an isomerisation of the product thus obtained leading to the branching of the hydrocarbon chain and to an enhancement of the properties of the paraffin at low temperatures.

During the HDO step, the hydrogen and the raw material of biological origin are passed over a hydrodeoxygenation catalytic bed in a simultaneous or in counter-current manner. During the HDO step, the pressure and the temperature are comprised between 20 and 150 bars and between 200 and 500° C. respectively. Conventional and known hydrodeoxygenation catalysts are used during this step. Optionally, the raw material of biological origin may be subjected to a process of prehydrogenation under mild conditions in order to avoid the side reactions of the double bonds prior to the HDO step. After the hydrodeoxygenation step, the product resulting from the reaction is subjected to an isomerisation step (ISO) where the hydrogen and the product, and optionally a mixture of n-paraffins, are passed over the catalytic beds for isomerisation in a simultaneous or counter-current manner. During the ISO step, the pressure and the temperature are comprised between 20 and 150 bars and between 200 and 500° C. respectively. Conventional and known isomerisation catalysts are used during this step.

Various different HDO/ISO methods are described in the literature. The application WO 2014/033762 describes a method comprising a pre-hydrogenation step, a hydrodeoxygenation (HDO) step, and an isomerisation step that are run counter-current. The patent application EP 1728844 describes a hydrocarbon compound production method for producing hydrocarbon compounds from a mixture of compounds of plant and animal origin.

Additional secondary processes may also be implemented (such as intermediate admixing, trapping, or other such processes).

The adjuvant composition according to the invention preferably comprises a hydrocarbon oil content ranging from 40 to 99% by weight, preferentially from 60 to 98% by weight and more preferentially from 85 to 96% by weight relative to the total weight of the adjuvant composition.

Surfactant:

The adjuvant composition according to the invention constitutes a fatty phase which, in order to form a vaccine, may be mixed with an aqueous phase comprising an antigen. The surfactant present in the adjuvant composition makes it possible to mix the fatty phase and the aqueous phase, which are immiscible, in order to obtain a homogeneous and stable mixture.

According to one embodiment of the invention, the adjuvant composition comprises between 2 and 10% by weight of surfactant, preferably between 4 and 8% by weight, preferably approximately 6% by weight of surfactant, relative to the total weight of the adjuvant composition.

The term 'surfactant' is understood to refer to one or more surfactants.

The surfactants that may be used in the invention are surfactants which are commercially available and accessible to the person skilled in the art. These are typically pharmaceutically acceptable surfactants that, in particular, are compatible for administration in humans and animals.

According to one embodiment of the invention, the surfactant contained in the adjuvant composition is a non-ionic surfactant.

According to one embodiment of the invention, the surfactant contained in the adjuvant composition is selected from among sorbitan esters, polyethoxylated sorbitan esters, mannitan esters, polyethoxylated mannitan esters; preferably from among sorbitan esters.

According to one embodiment of the invention, the surfactant contained in the adjuvant composition is a sorbitan fatty acid ester selected from among sorbitan oleate, sorbitan stearate, sorbitan palmitate, and sorbitan laurate. Preferably, the surfactant is a sorbitan monooleate. A non-limiting example of a surfactant that may be used in the adjuvant composition according to the invention is SPAN® 80 marketed by Croda.

According to another embodiment of the invention, the surfactant contained in the adjuvant composition is selected from among lecithins, polyethoxylated alkanols, polyethylene glycol esters, polyglycol polyhydroxystearates or polyglycerol polyhydroxystearates.

Adjuvant Composition According to the Invention

The adjuvant composition according to the invention comprises at least one hydrocarbon oil as defined here above and at least one surfactant.

According to one embodiment of the invention, the adjuvant composition consists of one or more hydrocarbon oil(s) as defined here above and one or more surfactants.

According to one embodiment of the invention, the adjuvant composition comprises at least one other oil that is different from the hydrocarbon oil defined in the present invention. Preferably, according to this embodiment, the adjuvant composition comprises from 1 to 40% by weight, preferably from 5 to 30% by weight, or indeed even from 10 to 20% by weight of another oil, relative to the total weight of the adjuvant composition.

Among the other oils, mention may be made of mineral-, plant-, or animal oils. In particular, the other oil may be a hydrocarbon oil derived from fossil or renewable sources, or a hydrogenated or non-hydrogenated plant oil.

According to one embodiment, the adjuvant composition according to the invention comprises another oil selected from among n-paraffins, typically from among n-paraffins comprising from 12 to 40 carbon atoms, preferably from 14 to 30 carbon atoms, or indeed even from 16 to 24 carbon atoms. The n-paraffins may be selected from among bio-sourced n-paraffins. These n-paraffins may be commercially available.

According to one embodiment of the invention, the adjuvant composition for a vaccine consists of, relative to the total weight of the adjuvant composition:

at least 40% by weight of one or more hydrocarbon oil(s) comprising a content by weight of isoparaffins ranging from 90 to 100% relative to the total weight of the hydrocarbon oil, said isoparaffins including, relative to the total weight of the isoparaffins, at least 20% by weight of isoparaffins having 17 carbon atoms or 18 carbon atoms;

from 1 to 15% by weight of one or more surfactant(s); and from 1 to 40% by weight of one or more other oil(s).

According to one embodiment of the invention, the adjuvant composition for a vaccine comprises, preferably consists of, relative to the total weight of the adjuvant composition:

at least 40% by weight of one or more hydrocarbon oil(s) comprising a content by weight of isoparaffins ranging from 90 to 100% relative to the total weight of the hydrocarbon oil, said isoparaffins including, relative to the total weight of the isoparaffins, at least 20% by weight of isoparaffins having 17 carbon atoms or 18 carbon atoms;

from 1 to 15% by weight of one or more surfactant(s); and from 1 to 40% by weight of one or more other oil(s) selected from among n-paraffins.

According to one embodiment, the adjuvant composition for a vaccine according to the invention comprises a mass ratio of hydrocarbon oil(s) defined in the invention/n-paraffin(s) that ranges from 60/40 to 99/1, preferably from 70/30 to 98/2, or indeed even from 80/20 to 95/5.

According to another embodiment of the invention, the adjuvant composition does not comprise any oil other than the hydrocarbon oil defined in the present invention.

According to one embodiment of the invention, the adjuvant composition for a vaccine consists of, relative to the total weight of the adjuvant composition:

at least 40% by weight of one or more hydrocarbon oil(s) comprising a content by weight of isoparaffins ranging from 90 to 100% relative to the total weight of the hydrocarbon oil, said isoparaffins including, relative to the total weight of the isoparaffins, at least 2% by weight, preferably at least 20% by weight of isoparaffins having 17 carbon atoms or 18 carbon atoms; and from 1 to 15% by weight of sorbitan esters, preferably sorbitan monooleate.

The adjuvant composition may also comprise other agents such as, for example, metal salts, preferably aluminum salts, preferably in an amount ranging from 0.1 to 5% by weight relative to the total weight of the adjuvant composition.

These metal salts make it possible to increase the viscosity of the adjuvant composition and to enhance the stability of the emulsion.

According to one embodiment of the invention, the adjuvant composition for a vaccine comprises, or indeed even consists of, relative to the total weight of the adjuvant composition:

at least 40% by weight of one or more hydrocarbon oil(s) comprising a content by weight of isoparaffins ranging from 90 to 100% relative to the total weight of the hydrocarbon oil, said isoparaffins including isoparaffins having 17 carbon atoms or 18 carbon atoms;

from 1 to 15% by weight of one or more surfactant(s); and optionally from 0.1 to 5% by weight of metal salts, preferably of aluminum salts;

optionally from 1 to 40% by weight of one or more other oil(s).

According to one embodiment of the invention, the adjuvant composition for a vaccine comprises, or indeed even consists of, relative to the total weight of the adjuvant composition:

at least 40% by weight of one or more hydrocarbon oil(s) comprising a content by weight of isoparaffins ranging from 90 to 100% relative to the total weight of the hydrocarbon oil, said isoparaffins including isoparaffins having 17 carbon atoms or 18 carbon atoms;

from 1 to 15% by weight of one or more surfactant(s); and optionally from 0.1 to 5% by weight of metal salts, preferably of aluminum salts;

optionally from 1 to 40% by weight of one or more other oil(s) selected, for example, from among n-paraffins.

According to another embodiment, the adjuvant composition further comprises a preservative, for example a paraben, preferably methylparaben, ethylparaben and/or propylparaben.

According to another embodiment, the adjuvant composition for a vaccine does not comprise metal salts.

According to one embodiment of the invention, the adjuvant composition does not comprise a polymer.

Vaccine Prepared from the Adjuvant Composition According to the Invention

The adjuvant composition according to the invention is useful for preparing a vaccine.

According to one embodiment, the vaccine is in the form of an emulsion, in which the adjuvant composition of the invention constitutes the fatty phase.

According to one particular embodiment, the vaccine according to the invention does not comprise a fatty phase other than the adjuvant composition according to the invention.

According to one embodiment, the vaccine is in the form of an emulsion, in which the aqueous phase comprises water, an antigen and a surfactant.

The surfactant contained in the aqueous phase may be identical or different from the surfactant contained in the adjuvant composition that constitutes the fatty phase. According to one embodiment of the invention, the surfactant contained in the aqueous phase is selected from among non-ionic surfactants, preferably from among sorbitan esters, polyethoxylated sorbitan esters, mannitan esters, polyethoxylated mannitan esters; preferably from among sorbitan esters.

According to one embodiment of the invention, the surfactant contained in the aqueous phase is a sorbitan fatty acid ester selected from among sorbitan oleate, sorbitan stearate, sorbitan palmitate and sorbitan laurate. Preferably, the surfactant is a polyethoxylated sorbitan ester. A non-limiting example of a surfactant that may be used in the aqueous phase of the vaccine according to the invention is Tween® 80 marketed by Croda.

According to another embodiment of the invention, the surfactant contained in the aqueous phase is selected from among lecithins, polyethoxylated alkanols, polyethylene glycol esters, polyglycol polyhydroxystearates or polyglycerol polyhydroxystearates.

According to one embodiment, the vaccine is in the form of a water-in-oil emulsion.

According to one embodiment, the vaccine is in the form of an emulsion in which the mass ratio between the aqueous phase and the fatty phase ranges from 50/50 to 10/90, preferably from 40/60 to 20/80, and more preferentially is 30/70.

Typically, the vaccine according to the invention has a dynamic viscosity at 25° C. of between 10 and 150 mPa·s, preferably between 15 and 120 mPa·s, preferably between 20 and 100 mPa·s, as measured according to the standard ASTM D445.

According to one embodiment, the vaccine is prepared by bringing the adjuvant composition according to the invention into contact with an aqueous solution comprising an antigen. The term 'antigen' is understood to refer to any substance that the immunological system of an individual recognises as foreign, and which provokes a response through the production of antibodies. The antigens are generally polysaccharides, polysaccharide derivatives, proteins or protein derivatives.

According to one embodiment, the antigen present in the vaccine is selected from among an anti-Foot and Mouth Disease virus, an anti-Pasteurella bacterium, a Newcastle antigen, an Avian Influenza antigen.

According to one particular embodiment, the vaccine is prepared by bringing the adjuvant composition according to the invention into contact with an aqueous phase comprising an antigen and a surfactant.

The inventors have discovered that the hydrocarbon oil according to the invention makes it possible to enhance the anti-infective effect of an antigen.

The present invention thus relates to the use of the hydrocarbon oil defined in the present invention, in an adjuvant composition, for enhancing the anti-infective effect of said adjuvant composition for a vaccine. The adjuvant composition, in the context of use, will preferably exhibit one or more of the characteristic features defined here above for the adjuvant composition according to the invention.

The present invention also relates to the use of the hydrocarbon oil according to the invention, in an adjuvant composition for a vaccine, for reducing the cytotoxicity of the vaccine.

The present invention also relates to the use of the hydrocarbon oil defined in the present invention, in an adjuvant composition for a vaccine, for enhancing the stability of the vaccine, in particular for a vaccine in the form of an emulsion.

EXAMPLES

In the remainder of the present description, examples are provided by way of illustration of the present invention and are in no way intended to limit the scope thereof.

Example 1: Evaluation of the Immunological Effects

Table 1 here below groups together the physicochemical properties of two hydrocarbon oils that may be used in adjuvant compositions according to the invention.

TABLE 1

| Characteristics | Oil A | Oil B |
|---|---|---|
| Aromatics (ppm) | <20 | <20 |
| Sulfur (ppm) | 0.1 | 0.11 |
| % iso paraffins (w/w) | 95.1 | 96.2 |
| % n-paraffins (w/w) | 4.9 | 3.8 |
| % naphthenics (w/w) | 0 | 0 |
| C13 (iso) | 0 | 0 |
| C14 (iso) | 0.12 | 0 |
| C15 (iso) | 11.45 | 0 |
| C16 (iso) | 47.89 | 1.58 |
| C17 (iso) | 18.57 | 14.17 |
| C18 (iso) | 17.07 | 79.69 |
| C19 (iso) | 0 | 0.12 |
| C20 (iso) | 0 | 0.38 |
| C27 (iso) | 0 | 0.29 |
| Quantity of carbon of biological origin (%) | >97 | >98 |
| Initial boiling point (° C.) | 259.5 | 293.6 |
| 5% Boiling point (° C.) | 270.2 | 296.7 |
| 50% Boiling point (° C.) | 274.5 | 298.5 |
| 95% Boiling point (° C.) | 286.4 | 305.3 |
| Final boiling point (° C.) | 287.5 | 324.1 |
| OECD biodegradability (28 days) (%) | 83 | 83 |
| Refractive index at 25° C. | 1.4357 | 1.4394 |
| Density at 15° C. (kg/m3) | 780.3 | 787.2 |
| Flash point (° C.) | 125 | 149 |
| Kinematic Viscosity at 40° C. (cSt) | 2.94 | 3.87 |
| Vapour pressure at 20° C. (kPa) | <0.01 | <0.01 |
| Aniline point (° C.) | 91 | 93.2 |

The following standards and methods were used to measure the properties presented here above:

flash point: EN ISO 2719 density at 15° C.: EN ISO 1185 viscosity at 40° C.: EN ISO 3104 aniline point: EN ISO 2977

Boiling point: ASTM D86 biodegradability: method OECD 306 refractive index at 20° C.: ASTM D 1218 vapour pressure: calculated according to methods well known to the person skilled in the art.

Example 2: Evaluation of the Immunological Effect of the Oils of Example 1

Oils A and B described in Example 1 were tested in vitro in order to determine the immunological effects thereof on human immune cells.

The immunological effects of the oils according to the invention were compared with those of reference adjuvants, in particular the hydrocarbon oils, Marcol™ 52 and Creasil IH CG, the latter being an isoparaffinic oil. The effects of the oils have also been compared to those of aluminum hydroxide, a reference adjuvant used in many commercial vaccines.

Various tests have been carried out on human immune cells. The first test was done on mononuclear cells isolated from peripheral blood (peripheral blood mononuclear cells or PBMC) of healthy donors. Other tests were then carried out on macrophages and dendritic cells obtained by separating the lymphocyte and monocyte populations of PBMCs and by differentiating the monocytes in vitro into macrophages or dendritic cells under the effect of cytokines (GM-CSF & M-CSF or interleukin (IL)-4). These cell models are well described in the scientific literature, in particular for characterising the immunological effects of candidate vaccines and their constituents such as the adjuvants thereof.

The PBMCs, macrophages and dendritic cells were brought into contact for 24 hours with the oils according to the invention as well as with the reference adjuvants. The ability of cells to multiply, die and differentiate was measured by assaying cell activation, cell viability, cytokine profile and membrane expression of other biomarkers.

Preparation of culture microplates: 24 hours prior to incubation with the oils, the cells are seeded in 96-well microplates (Corning). The microplates are then placed in the incubator at 37° C.

Incubation of cells with oils: the incubation time duration was 15 minutes. After these incubation times, the microplates are emptied and the cells are rinsed.

Measurement of cell activation and cell viability: 3 days after treatment with the oils, the cells are observed under a microscope in order to assess cell activation and then subjected to a colorimetric test with methyl tetrazolium salt (MTT) in order to assess the cell viability.

Cytokine assay: 5 days after the treatment with the oils, multiplexed enzyme immunoassays are carried out and immunophenotyping analysis is performed by means of flow cytometry in order to determine the cytokine profile and the membrane expression of the cells.

The effects were measured with respect to 2 or 3 donors, in triplicate cultures. The test results are presented in Tables 2-10 here below.

The results of the observations relating to cell viability and activation at various different dilutions (the dilutions are expressed in % by volume) are presented in FIGS. 1 to 3. A significant cell activation is observed for Oils A and B with a greater increase for Oil A than for Oil B.

Under these experimental conditions, Marcol™ 52 and Creasil® IH CG present the same profile since they reduce the viability of PBMCs, macrophages and dendritic cells derived from different cell donors. Marcol™ 52 and Creasil® IH CG exhibit cytotoxicity at low dilutions (dilutions expressed in % by volume), that is to say at high concentrations. On the other hand, Oils A and B, just like aluminum hydroxide, do not induce a decrease in cell viability. Unlike Marcol™ 52 and Creasil® IH CG, Oils A and B show no cytotoxicity at the concentrations tested.

The cytokine profile of PBMCs is observed after or without antigenic stimulation either with the aid of Tetanus Toxin (TT) or tuberculin (PPD).

Table 2, here below, presents the compiled results of the assays of the cytokines after 5 days in the supernatants of PBMC cultures not exposed in parallel to an antigen. The results are expressed in pg/mL.

Cytokine Profile of PBMCs

Without antigenic stimulation of PBMCs, modulations are observed at the level of cytokine production in the presence of the various adjuvants tested. Under these experimental conditions, Oil A is distinguished from other adjuvants by a more pronounced decrease in the level of IL-5, a decrease in that of TNF-$\alpha$ and an absence of increase in IFN-$\gamma$.

The cytokine profile of macrophages and dendritic cells was assessed during the mixed lymphocyte reactions (MLR).

Macrophages

Table 3 here below, compares the effects of adjuvants on lymphocyte proliferation in response to interactions with macrophages, whether or not with antigen (purified protein derivative PPD). The results are expressed as a percentage relative to the untreated cells (Control).

TABLE 3

| | | Without PPD | | With PPD | |
|---|---|---|---|---|---|
| | % or Dilution | Mean | Standard Deviation. | Mean | Standard Deviation. |
| Control | | 100 | 12 | 100 | 12 |
| Aluminum | 10% | 74 | 7 | 63 | 7 |
| hydroxide | 2% | 68 | 6 | 61 | 12 |
| Oil A | 4 | 109 | 14 | 121 | 11 |
| | 20 | 145 | 7 | 110 | 13 |
| | 100 | 131 | 5 | 119 | 5 |
| Marcol ™ 52 | 20 | 108 | 9 | 78 | 8 |
| | 100 | 102 | 7 | 48 | 7 |
| | 500 | 103 | 6 | 88 | 8 |
| Creasil ® IH CG | 50 | 107 | 7 | 98 | 6 |
| | 250 | 116 | 6 | 98 | 5 |
| | 1250 | 107 | 6 | 103 | 4 |
| Oil B | 4 | 100 | 2 | 98 | 11 |
| | 20 | 171 | 7 | 136 | 17 |
| | 100 | 135 | 4 | 123 | 6 |

Cytokine Profile of Macrophages with and without Prior Antigen (PPD) Presentation Table 4 here below, details the effects of adjuvants on cytokine levels in the culture supernatants of macrophages co-cultured with autologous lymphocytes and without prior antigen (PPD) presentation.

TABLE 2

| | Dilution | IL-2 | IL-4 | IL-5 | IL-10 | IL-12 | IL-13 | GM-CSF | IFN-γ | TNF-α |
|---|---|---|---|---|---|---|---|---|---|---|
| Control | | 4 978 | 14 | 185 | 48 | 3 | 2 003 | 227 | 750 | 71 445 |
| Aluminum hydroxide | | 4 104 | 6 | 33 | 53 | 1 | 645 | 121 | 538 | 9 262 |
| Oil A | 4 | 3 842 | 12 | 65 | 71 | 3 | 2 052 | 188 | 992 | 41 643 |
| | 20 | 4 043 | 9 | 35 | 24 | 2 | 1 175 | 130 | 515 | 25 561 |
| | 100 | 3 991 | 11 | 72 | 28 | 2 | 1 698 | 155 | 382 | 35 206 |
| Marcol ™ 52 | 20 | 3 852 | 6 | 14 | 7 | 1 | 348 | 16 | 72 | 15 851 |
| | 100 | 4 886 | 14 | 181 | 1 | 3 | 1 896 | 227 | 1 445 | 69 664 |
| | 500 | 5 067 | 14 | 294 | 68 | 2 | 2 773 | 283 | 1 192 | 71 217 |
| Creasil ® IH CG | 50 | 4,662 | 1 | 2 | 3 | 0 | 7 | 3 | 13 | 1 987 |
| | 250 | 4 807 | 12 | 155 | 41 | 3 | 2 312 | 266 | 1 091 | 40 023 |
| | 1250 | 4 535 | 14 | 211 | 55 | 3 | 2 200 | 286 | 1 107 | 70 288 |
| Oil B | 4 | 3 708 | 13 | 63 | 43 | 2 | 1 089 | 140 | 789 | 64 724 |
| | 20 | 4 761 | 13 | 99 | 36 | 3 | 1 673 | 202 | 1 242 | 75 070 |
| | 100 | 5 240 | 14 | 133 | 50 | 2 | 1 734 | 190 | 1 323 | 75 138 |

TABLE 4

| | % or Dilution | IL-2 | IL-4 | IL-5 | IL-10 | IL-12 | IL-13 | GM-CSF | IFN-γ | TNF-α |
|---|---|---|---|---|---|---|---|---|---|---|
| NT | | 24 | 0 | 1 | 3 | 0.01 | 1 | 1 | 1 | 442 |
| Aluminum hydroxide | 10 | 9 | 0 | 0.56 | 3 | 0.01 | 0 | 1 | 1 | 341 |
| Oil A | 4 | 37 | 0 | 0.04 | 7 | 0 | 1 | 2 | 1 | 1 331 |
| | 20 | 37 | 1 | 0.56 | 5 | 0.26 | 0 | 3 | 1 | 2 222 |
| | 100 | 25 | 0 | 0.56 | 4 | 0.01 | 0 | 1 | 1 | 1 091 |
| Marcol ™ | 20 | 10 | 0 | 0.04 | 2 | 0 | 0.14 | 0 | 0.68 | 295 |
| | 100 | 7 | 0 | 0.31 | 1 | 0 | 0 | 0.21 | 0.31 | 227 |
| | 500 | 15 | 0 | 0.04 | 4 | 0.26 | 0.14 | 1 | 0.31 | 416 |
| Creasil ® | 50 | 22.5 | 0.11 | 0.04 | 4 | 0 | 0 | 1 | 0.68 | 802 |
| IH CG | 250 | 18 | 0.11 | 0 | 3 | 0 | 0 | 1 | 0.31 | 612 |
| | 1250 | 15 | 0.11 | 0.56 | 4 | 0 | 0.14 | 0.38 | 1 | 564 |
| Oil B | 4 | 16 | 0.11 | 0.81 | 6 | 0 | 0.14 | 1 | 0.68 | 659 |
| | 20 | 21 | 0 | 0.04 | 4 | 0.14 | 0 | 1 | 0.68 | 1 121 |
| | 100 | 20 | 0 | 0 | 4 | 0 | 0 | 1 | 0.68 | 579 |

Table 5 here below, details the effects of adjuvants on cytokine levels in culture supernatants of macrophages co-cultured with autologous lymphocytes and after antigen (PPD) presentation.

TABLE 5

| | % or Dilution | IL-2 | IL-4 | IL-5 | IL-10 | IL-12 | IL-13 | GM-CSF | IFN-γ | TNF-α |
|---|---|---|---|---|---|---|---|---|---|---|
| NT | | 18 | 0 | 2 | 4 | 0 | 1 | 1 | 1 | 235 |
| PPD | | 297 | 6 | 12 | 16 | 0 | 41 | 144 | 20 | 15 356 |
| Aluminum hydroxide | 10 | 462 | 11 | 28 | 24 | 3 | 117 | 777 | 43 | 63 154 |
| Oil A | 4 | 690 | 19 | 59 | 36 | 3 | 132 | 999 | 62 | 66 323 |
| | 20 | 539 | 15 | 37 | 39 | 2 | 15 | 522 | 12 | 43 879 |
| | 100 | 613 | 16 | 40 | 39 | 3 | 56 | 604 | 21 | 49 185 |
| Marcol ™ 52 | 20 | 328 | 7 | 11 | 1 | 1 | 15 | 128 | 15 | 13 816 |
| | 100 | 357 | 8 | 18 | 13 | 1 | 38 | 219 | 31 | 19 957 |
| | 500 | 411 | 10 | 2 | 17 | 1 | 59 | 236 | 28 | 20 938 |
| Creasil ® | 50 | 505 | 12 | 30 | 26 | 1.5 | 79 | 435 | 31 | 32 987 |
| IH CG | 250 | 544 | 14 | 31 | 24 | 1.5 | 69 | 385 | 31 | 32 601 |
| | 1250 | 512 | 13 | 27 | 22 | 2 | 70 | 373 | 31 | 32 061 |
| Oil B | 4 | 566 | 14 | 40 | 36 | 2 | 326 | 492 | 87 | 36 840 |
| | 20 | 454 | 11 | 21 | 16 | 1.5 | 37 | 252 | 28 | 23 104 |
| | 100 | 492 | 11 | 22 | 20 | 1 | 96 | 273 | 21 | 25 019 |

The results of the cytokine assays indicate that the presence of Oil A induces increased production of IL-2, IL-10, IL-12 and TNF-α. These results suggest a cellular Th1 response, that is favoured over a Th2 profile. The presence of IL-12 directs the differentiation of naive T lymphocytes into lymphocytes with a Th1 profile. However, the detection of cytokines such as IL-4 and L-13 is indicative of a mixed Th1 and Th2 profile or of a regulation between the two profiles. The high production of GM-CSF by Oils A and B is also an element that can accelerate a microbial response. In fact, the GM-CSF, at the central and peripheral levels, increases the number or the functionality of cells of the monocyte/macrophage lineage, thus potentiating the anti-infectious responses.

Dendritic Cells

Table 6 here below, compares the effects of adjuvants on lymphocyte proliferation in response to interactions with dendritic cells, whether or not with antigen (purified protein derivative PPD). The results are expressed as a percentage relative to the untreated cells (Control).

TABLE 6

| | | Without PPD | | With PPD | |
|---|---|---|---|---|---|
| | % or Dilution | Mean | Standard Deviation. | Mean | Standard Deviation. |
| Control | | 100 | 4 | 100 | 9 |
| Aluminum | 10% | 57 | 28 | 69 | 1 |
| hydroxide | 2% | 96 | 12 | 106 | 5 |
| Oil A | 4 | 128 | 5 | 131 | 11 |
| | 20 | 135 | 2 | 147 | 8 |
| | 100 | 138 | 6 | 138 | 7 |
| Marcol ™ 52 | 20 | 114 | 4 | 137 | 5 |
| | 100 | 114 | 2 | 124 | 5 |
| | 500 | 118 | 13 | 114 | 4 |
| Creasil ® IH CG | 50 | 96 | 41 | 107 | 2 |
| | 250 | 128 | 3 | 141 | 14 |
| | 1250 | 108 | 1 | 116 | 5 |
| Oil B | 4 | 79 | 3 | 87 | 4 |
| | 20 | 161 | 0 | 177 | 2 |
| | 100 | 124 | 2 | 134 | 2 |

Table 7 details the effects of adjuvants on the cytokine levels in the culture supernatants of dendritic cells co-cultured with autologous lymphocytes and without prior antigen (PPD) presentation.

TABLE 7

| | % or Dilution | IL-2 | IL-4 | IL-5 | IL-10 | IL-12 | IL-13 | GM-CSF | IFN-g | TNF-a |
|---|---|---|---|---|---|---|---|---|---|---|
| NT | | 37 | 0.1 | 0.6 | 5.5 | 0 | 7.5 | 2.5 | 1 | 477 |
| Aluminum hydroxide | 10 | 45 | 0.1 | 1 | 8 | 0 | 10 | 3 | 1 | 649 |
| Oil A | 4 | 51 | 0.5 | 1 | 7 | 0.1 | 12 | 8 | 5 | 1 354 |
| | 20 | 31 | 0.1 | 0.6 | 5 | 0 | 2.5 | 9 | 4 | 1 417 |
| | 100 | 37 | 0.1 | 1 | 6 | 0 | 6 | 7 | 3 | 1 059 |
| Marcol ™ 52 | 20 | 31 | 0 | 1 | 5 | 0 | 6 | 2 | 1.5 | 504 |
| | 100 | 37 | 0 | 0.6 | 6 | 0 | 9.5 | 3 | 2 | 626 |
| | 500 | 24.5 | 0.1 | 0.6 | 2 | 0 | 3 | 10 | 4.5 | 1 214 |
| Creasil ® IH CG | 50 | 39 | 0.3 | 0.3 | 2 | 0 | 3 | 9 | 7 | 1 246 |
| | 250 | 37 | 0.1 | 0 | 5 | 0 | 8 | 5 | 3 | 828 |
| | 1250 | 47 | 0 | 0.6 | 6 | 0 | 11 | 4 | 2 | 722 |
| Oil B | 4 | 47 | 0.3 | 0 | 8 | 0 | 11 | 4 | 3 | 742 |
| | 20 | 23.5 | 0 | 0.04 | 8 | 0 | 3 | 3.5 | 3 | 925 |
| | 100 | 45.5 | 0.1 | 1.5 | 8.5 | 0 | 11 | 4 5 | | 2629 |

Table 8 details the effect of adjuvants on cytokine levels in culture supernatants of dendritic cells co-cultured with autologous lymphocytes and after antigen (PPD) presentation.

TABLE 8

| | % or Dilution | IL-2 | IL-4 | IL-5 | IL-10 | IL-12 | IL-13 | GM-CSF | IFN-γ | TNF-α |
|---|---|---|---|---|---|---|---|---|---|---|
| NT | | 40 | 0 | 0.5 | 7 | 0 | 10 | 4 | 2 | 322 |
| PPD | | 771 | 7 | 31 | 47 | 3 | 770 | 205 | 779 | 12 854 |
| Aluminum hydroxide | 10 | 686 | 9 | 38 | 69 | 3 | 1 016 | 263 | 961 | 14 338 |
| Oil A | 4 | 1 189 | 14 | 43 | 86 | 5 | 617 | 465 | 1 689 | 22 704 |
| | 20 | 617 | 7 | 21 | 46 | 3 | 96 | 237 | 218 | 14 527 |
| | 100 | 913 | 9 | 21 | 56 | 3 | 257 | 260 | 438 | 15 487 |
| Marcol ™ 52 | 20 | 855 | 8 | 29 | 52 | 4 | 737 | 226 | 854 | 14 731 |
| | 100 | 770 | 9 | 35 | 67 | 3 | 917 | 241 | 851 | 15 248 |
| | 500 | 778 | 9 | 33 | 75 | 4 | 875 | 240 | 974 | 14 630 |
| Creasil ® IH CG | 50 | 1 003 | 10 | 33 | 78 | 4 | 657 | 304 | 1 032 | 17 861 |
| | 250 | 1 031 | 10 | 47 | 72 | 4 | 1 809 | 429 | 1 026 | 17 150 |
| | 1250 | 951 | 9 | 33 | 63 | 4 | 769 | 265 | 893 | 17 289 |
| Oil B | 4 | 987 | 12 | 50 | 106 | 5 | 1 467 | 361 | 2 019 | 22 056 |
| | 20 | 843 | 9 | 28 | 57 | 4 | 526 | 266 | 1 490 | 16 369 |
| | 100 | 860 | 8 | 34 | 53 | 3 | 795 | 248 | 1 134 | 15 296 |

The cytokine assays in the culture supernatants indicate that Oils A and B, and in particular Oil A, direct the response to a Th1 profile with increased levels of TNF-α, IFN-γ, and IL-2. As with the macrophages, an increase in the level of GM-CSF is observed. Oils A and B are distinguished from the other adjuvants tested at the cytokine level. In fact, the three other adjuvants generate little or no modulations of the cytokines tested.

Oils A and B promote the proliferation/activation of the lymphocytes that are brought into contact with the cells presenting antigens, regardless of whether they are macrophages or dendritic cells, whether or not in the presence of an antigen such as PPD.

Membrane Expression

Macrophages

TABLE 9

| | Aluminum hydroxide | Oil A | Marcol ™ 52 | Creasil ® IH CG | Oil B |
|---|---|---|---|---|---|
| CD80 | = | – | – | – | = |
| CD86 | = | = | = | = | – |
| CD163 | – | – – – | = | – – – | = |
| CD16 | – | – | = | – | – |

TABLE 9-continued

| | Aluminum hydroxide | Oil A | Marcol ™ 52 | Creasil ® IH CG | Oil B |
|---|---|---|---|---|---|
| CD32 | – | – | = | – | – |
| CD64 | = | + | = | + | – |
| CD14 | – | – | = | – | – |
| HLA-DR | = | – | = | – | = |

Effects of Adjuvants on the Differentiation of Macrophages (Immunophenotyping and Analysis 3 Days after the Treatment Process).

The effect of Oils A and B on the membrane expression of macrophages is close to that of Creasil® IH CG with a significant decrease in the proteins CD163 and CD32 (Cluster of Differentiation), one of the Fc (Fragment Crystallisable) receptors of immunoglobulins. This double modulation seems to be indicative of the biasing of the macrophages to a pro-inflammatory profile of type M1, that is favourable to a beneficial inflammatory response of the host against a microbial infection. This biasing is consistent with cytokine production levels, such as that of TNF-α, described for activating M1-biased macrophages, and that of IL-12, secreted by the same M1 macrophages. At the same time, it should be noted that the effects of aluminum hydroxide (decrease in the expression of CD14 and increase in the expression of CD86) are identical to those previously described by the laboratory (Rimaniol & al., *In vitro interactions between macrophages and aluminum-containing adjuvants. Vaccine*, 2007, 25, 6784-6792). These results make it possible to establish the modulations observed with Oils A and B.

Dendritic Cells

TABLE 10

|  | Aluminum hydroxide | Oil A | Marcol ™ 52 | Creasil ® IH CG | Oil B |
|---|---|---|---|---|---|
| CD1a | --- | = | = | = | = |
| HLA-DR | = | = | - | - | + |
| CD83 | ++ | ++ | = | - | + |
| CD40 | = | = | = | = | = |

Effects of Adjuvants on the Differentiation of Dendritic Cells. (Immunophenotyping and Analysis 3 Days after the Treatment Process).

With regard to the membrane markers of dendritic cells, Oils A and B have a specific profile. On the one hand, they do not modulate the dendritic cell specific expression of CD1a. On the other hand, Oils A and B, and in particular Oil A, increase the expression of CD83, a dendritic cell maturation marker.

In conclusion, Oils A and B exhibit a specific profile, biased to Th1 type responses for lymphocytes and M1 for macrophages. They also lead to maturation of dendritic cells. These profiles, like the increased macrophage synthesis of GM-CSF, are believed to promote an anti-infective response, a role expected of an adjuvant.

Example 3: Preparation of an Emulsion Comprising the Adjuvant Composition of the Invention—Evaluation of the Stability of the Emulsion An example of an emulsion comprising the adjuvant composition according to the invention is given in Table 11 here below. The percentages are percentages by weight relative to the total weight of the adjuvant composition.

TABLE 11

|  |  | Composition 1 | Composition 2 |
|---|---|---|---|
| Fatty phase | Oil | 63.37% | 63.37% |
|  | Surfactant: SPAN ® 80 | Oil A 4.00% | Marcol ™ 52 4.00% |
| Aqueous phase | Demineralised water | 31.30% | 31.30% |
|  | Surfactant: TWEEN ® 80 | 1.33% | 1.33% |

The operating procedure for preparing the emulsion is as follows:

The oil and the surfactant from the fatty phase are introduced into a test tube in the proportions indicated in Table 11. The test tube is agitated and heated to 80° C. until a homogeneous phase is obtained.

The water and the surfactant of the aqueous phase are introduced into a second test tube in the proportions indicated in Table 11. The test tube is agitated and heated to 80° C. until a homogeneous phase is obtained.

At 80° C., the aqueous phase is poured slowly into the fatty phase with vigorous agitation. Subsequently the emulsion is then mixed by means of a Turrax® type mixer at 9500 revolutions/minute for 30 seconds.

The mixture is left to cool to 25° C. with moderate agitation.

When the emulsion is produced, a single homogeneous phase is observed. The emulsion is then centrifuged at time T0, and subsequently after 24 hours for a period of 20 minutes at 3500 revolutions/minute with a centrifuge—Fisher Bioblock Scientific Sigma 1-6.

The stability of the composition described in Table 11 is observed visually after centrifugation at T0, after centrifugation after 24 hours (T24 h) and after 90 days (T2160 h).

The test tube contains 6.6 cm of emulsion, which comprises 4.2 cm of fatty phase. A manual measurement of the dephasing is performed, that is to say the measurement of the fatty phase that is released above the emulsion.

TABLE 12

|  | T0 | T24 h | T2160 h |
|---|---|---|---|
| Composition 1 | 0.1 cm | 0.3 cm | 4.2 cm |
| Composition 2 | 0.1 cm | 0.4 cm | 4.2 cm |

Measurement of the Release of the Fatty Phase

At T0, the same release is observed for the emulsion comprising the oil Marcol™ 52 as for the emulsion comprising the Oil A.

After 24 hours, the emulsion comprising the oil Marcol™ 52 has released more than the emulsion comprising the Oil A. It is observed that for the composition comprising Oil A, there is a release of 7.1% (=0.3/4.2) of fatty phase relative to the amount of total fatty phase comprised in the emulsion, against 9.5% (=0.4/4.2) for the composition comprising the oil Marcol™ 52.

Example 4: Preparation of a Vaccine Comprising the Adjuvant Composition of the Invention An example of a vaccine comprising the adjuvant composition according to the invention is provided in Table 13 here below.

TABLE 13

|  |  | Composition 1 | Composition 2 |
|---|---|---|---|
| Fatty phase: adjuvant composition | Oil | 132 g of Oil A | 132 g of Oil B |
|  | Surfactant: SPAN ® 80 | 8 g | 8 g |
| Aqueous phase containing the antigen | Water + antigen (Newcastle) | 57.5 g | 57.5 g |
|  | Surfactant: TWEEN ® 80 | 2.5 g | 2.5 g |

The vaccine is prepared according to the following protocol:

Preparation of the Fatty Phase:

Mix 132 g of hydrocarbon oil with 8 g of Span® 80 by means of a Turrax® type mixer set at 10,000 revolutions/minute for a period of 3 minutes at 25° C.

Preparation of the Aqueous Phase:

Mix 2.5 g of Tween® 80 with 57.5 g of an antigen solution by means of a Turrax® type mixer set at 10,000 revolutions/minute for a period of 3 minutes at 25° C.

Preparation of the Emulsion:

Introduce the fatty phase into a Turrax® type mixer, agitate for 30 seconds at 10,000 revolutions/minute, then add in the aqueous phase slowly over a period of 3 minutes while maintaining agitation at 10,000-12,000 revolutions/minute.

200 g of vaccine are thus obtained in the form of a water-in-oil emulsion.

The invention claimed is:

1. An adjuvant composition for a vaccine comprising, relative to the total weight of the adjuvant composition:

at least 40% by weight of hydrocarbon oil comprising a content by weight of isoparaffins ranging from 90 to 100% relative to the total weight of the hydrocarbon oil, said isoparaffins including:

isoparaffins having 16 carbon atoms, isoparaffins having 17 carbon atoms, and isoparaffins having 18 carbon atoms, in a combined amount ranging from 80 to 98% by weight, relative to the total weight of the hydrocarbon oil; or isoparaffins having 17 carbon atoms and isoparaffins having 18 carbon atoms, in a combined amount ranging from 80 to 98% by weight, relative to the total weight of the hydrocarbon oil; and from 1 to 15% by weight of one or more surfactant(s).

2. The composition according to claim 1, wherein said isoparaffins comprise, relative to the total weight of isoparaffins, at least 2% by weight of isoparaffins having 17 carbon atoms and/or isoparaffins having 18 carbon atoms.

3. The composition according to claim 1, wherein the surfactant is selected from among non-ionic surfactants.

4. The composition according to claim 1, wherein the surfactant is a sorbitan fatty acid ester.

5. The composition according to claim 1, comprising, relative to the total weight of the composition:

from 60 to 98% by weight of hydrocarbon oil comprising a content by weight of isoparaffins ranging from 95 to 100% relative to the total weight of the hydrocarbon oil, said isoparaffins including isoparaffins having 17 carbon atoms or 18 carbon atoms; and from 2 to 10% by weight of one or more surfactant(s).

6. The composition according to claim 1, further comprising an oil other than said hydrocarbon oil.

7. A vaccine comprising the adjuvant composition as defined in claim 1 and at least one antigen.

8. The vaccine according to claim 7, wherein the vaccine is in the form of a water-in-oil emulsion.

9. The vaccine according to claim 8, wherein the mass ratio between the aqueous phase and the fatty phase of the water-in-oil emulsion ranges from 50/50 to 10/90.

10. The composition according to claim 1, wherein the surfactant is selected from among sorbitan esters.

11. The composition according to claim 1, wherein the surfactant is a sorbitan monooleate.

12. The composition according to claim 6, wherein the oil other than said hydrocarbon oil is selected from among n-paraffins.

13. The composition according to claim 12, wherein the n-paraffins comprise from 14 to 30 carbon atoms.

14. The composition according to claim 12, exhibiting a mass ratio of hydrocarbon oil/n-paraffin that ranges from 60/40 to 99/1.

15. The vaccine according to claim 8, wherein the mass ratio between the aqueous phase and the fatty phase of the water-in-oil emulsion ranges from 40/60 to 20/80.

* * * * *